United States Patent
Takeda et al.

(10) Patent No.: US 8,522,786 B2
(45) Date of Patent: Sep. 3, 2013

(54) BRAIN COOLING APPARATUS AND FLUID INJECTION APPARATUS USED THEREFOR

(75) Inventors: Yoshimasa Takeda, Okayama (JP); Kiyoshi Morita, Okayama (JP)

(73) Assignee: National University Corporation Okayama University, Okayama (JP)

( * ) Notice: Subject to any disclaimer, the term of this patent is extended or adjusted under 35 U.S.C. 154(b) by 1775 days.

(21) Appl. No.: 11/547,421

(22) PCT Filed: Mar. 3, 2005

(86) PCT No.: PCT/JP2005/003636
§ 371 (c)(1),
(2), (4) Date: Sep. 29, 2006

(87) PCT Pub. No.: WO2005/097016
PCT Pub. Date: Oct. 20, 2005

(65) Prior Publication Data
US 2008/0086186 A1 Apr. 10, 2008

(30) Foreign Application Priority Data
Mar. 31, 2004 (JP) ................................. 2004-102719

(51) Int. Cl.
*A61H 3/04* (2006.01)
(52) U.S. Cl.
USPC ..................................... 128/207.14; 604/303
(58) Field of Classification Search
USPC .............. 128/207.14, 207.15, 200.26; 607/2; 604/103.04, 303
See application file for complete search history.

(56) References Cited

U.S. PATENT DOCUMENTS

| 4,091,816 | A | 5/1978 | Elam |
| 4,231,365 | A | 11/1980 | Scarberry |
| 4,509,514 | A | 4/1985 | Brain |
| 5,261,399 | A | 11/1993 | Klatz et al. |
| 5,653,229 | A | 8/1997 | Greenberg |
| 2003/0051734 | A1* | 3/2003 | Brain ........................ 128/207.15 |
| 2003/0233068 | A1* | 12/2003 | Jayaraman ................. 604/96.01 |

FOREIGN PATENT DOCUMENTS

| EP | 0 922 465 A2 | 6/1999 |
| GB | 2 328 879 A | 3/1999 |
| GB | 2328879 A * | 3/1999 |
| JP | 1-27751 B2 | 5/1989 |

(Continued)

OTHER PUBLICATIONS

European Communication with Supplementary European Search Report dated May 2, 2008 for application No. 05719940.8-2305 (3 pages).

(Continued)

*Primary Examiner* — Melanie Hand
(74) *Attorney, Agent, or Firm* — Osha Liang LLP

(57) ABSTRACT

A brain cooling apparatus includes a tube body 2 which can maintain an airway in the respiratory tract of a living body; a pharyngeal cuff 5 which is provided in the peripheral part of this tube body 2 and can store a cooled fluid; and an injection and discharge portion 6 which can inject and discharge a fluid into and from this pharyngeal cuff 5, in which the pharyngeal cuff 5 is flexible enough to inflate and deflate when a fluid is injected and discharged, and when a fluid is injected in a state where an airway in the respiratory tract of a living body is maintained by the tube body 2, the inflated pharyngeal cuff adheres closely to the pharyngeal part T of the living body.

9 Claims, 11 Drawing Sheets

(56) References Cited

FOREIGN PATENT DOCUMENTS

| | | |
|---|---|---|
| JP | 6-509001 | 10/1994 |
| JP | 11-206885 | 8/1999 |
| JP | 2000-60890 | 2/2000 |
| JP | 2002-542892 | 12/2002 |
| WO | 95/23624 | 9/1995 |
| WO | 98/23317 | 6/1998 |

OTHER PUBLICATIONS

International Search Report PCT/JP2005/003636 dated Jun. 7, 2005 (2 pages).
Patent Abstracts of Japan 2000-060890 dated Feb. 29, 2000 (2 pages).
U.S. Patent Application Publication No. 2001/0010011 A1 dated Jul. 26, 2001. Corresponds to JP 2002-542892.

* cited by examiner

BRAIN COOLING APPARATUS AND FLUID INJECTION APPARATUS USED THEREFOR

TECHNICAL FIELD

The present invention relates to a brain cooling apparatus.

BACKGROUND ART

In a living body such as the human body, when a respiratory function or a circulatory function becomes insufficient, such as cardiac arrest (hereinafter, referred to as a cardiac-arrest state), oxygen which is supplied to a brain falls short. This shortage of oxygen may kill brain cells. In other words, it is known that it may cause so-called ischemic neuronal damage.

Hence, with respect to a living body in the cardiac-arrest state, a treatment such as artificial respiration is given for resuscitating the living body from the cardiac-arrest state. However, even if this treatment resuscitates the living body from the cardiac-arrest state, the above described ischemic neuronal damage may give a sequela to the brain.

In view of such circumstances, in recent years, hypothermic therapy is proposed as a treatment for preventing ischemic neuronal damage from being caused. In such therapy, the brain is cooled by lowering the body temperature of a living body in the cardiac-arrest state.

The sooner the hypothermic therapy is given after ischemia has broken out, the more effective it will be. In other words, as time passes, its effect will lower rapidly.

As the hypothermic therapy, there is used a method of wrapping the whole body in a blanket or the like inside of which a cooling liquid circulates, so that the temperature of a living body can be lowered. Or, for example, as disclosed in Patent Document 1, a method of directly cooling a head of a living body is used by covering the head with a mask inside of which a cooling liquid circulates.

However, in the case where the blanket or the mask is used to lower the body temperature, the body is cooled from its surface. Thus, it takes time to lower the brain temperature, and in addition, it is difficult to cool the brain adequately up to its sub-cortical tissue.

Besides, if a living body is resuscitated from the cardiac-arrest state with the whole body cooled using the blanket, the temperature of the whole body may lower, thereby inducing arrhythmia. Therefore, close attention has to be paid to timing in cooling a living body using the blanket.

In view of the above described problems, it is an object of the present invention to provide a brain cooling apparatus which is capable of cooling the brain adequately up to its sub-cortical tissue within a short period of time.

Patent Document 1: Japanese Patent Laid-Open No. 2000-60890

SUMMARY OF INVENTION

In order to solve the above described problems, a brain cooling apparatus according to the present invention comprises: a tube-shaped member which is orally and nasally inserted so that an airway is maintained in a respiratory tract of the living body; a storage portion which is attached to the peripheral part of the tube-shaped member and stores a cooled fluid; and an injection and discharge portion which injects and discharges a fluid into and from the storage portion, wherein the storage portion is flexible enough to inflate and deflate when a fluid is injected and discharged, and when a fluid is injected in a state where an airway in the respiratory tract of the living body is maintained by the tube-shaped member, the inflated storage portion adheres closely to the pharyngeal part of the living body.

According to the present invention, a fluid is injected into the storage portion, with the tube-shaped member kept inserted in the living body. This allows the storage portion to adhere closely to the pharyngeal part. Thus, the pharyngeal part can be cooled by the cooled fluid inside of the storage portion. At and near the pharyngeal part, there are numerous blood vessels which supply blood to the brain. Therefore, the storage portion cools these blood vessels, thereby cooling the blood in the blood vessels and cooling the brain.

Hence, according to the present invention, the blood vessels which lie relatively close to the brain is cooled from the inside of the body (i.e., the pharyngeal part). This allows the brain to cool within a short period of time. In addition, the brain is cooled via blood, and thus, it can be cooled adequately up to its sub-cortical tissue.

Furthermore, according to the present invention, the brain is cooled by cooling only the pharyngeal part. Therefore, cares about when to cool the brain become smaller than in the case where the whole body is cooled.

Furthermore, according to the present invention, using the tube-shaped member, an airway is maintained in the respiratory tract of the living body. This makes it possible to simultaneously conduct a cardiac-arrest resuscitation treatment such as artificial respiration, and a hypothermic therapy.

DETAILED DESCRIPTION

Hereinafter, preferred embodiments of the present invention will be described with reference to the drawings.

Figure 1:
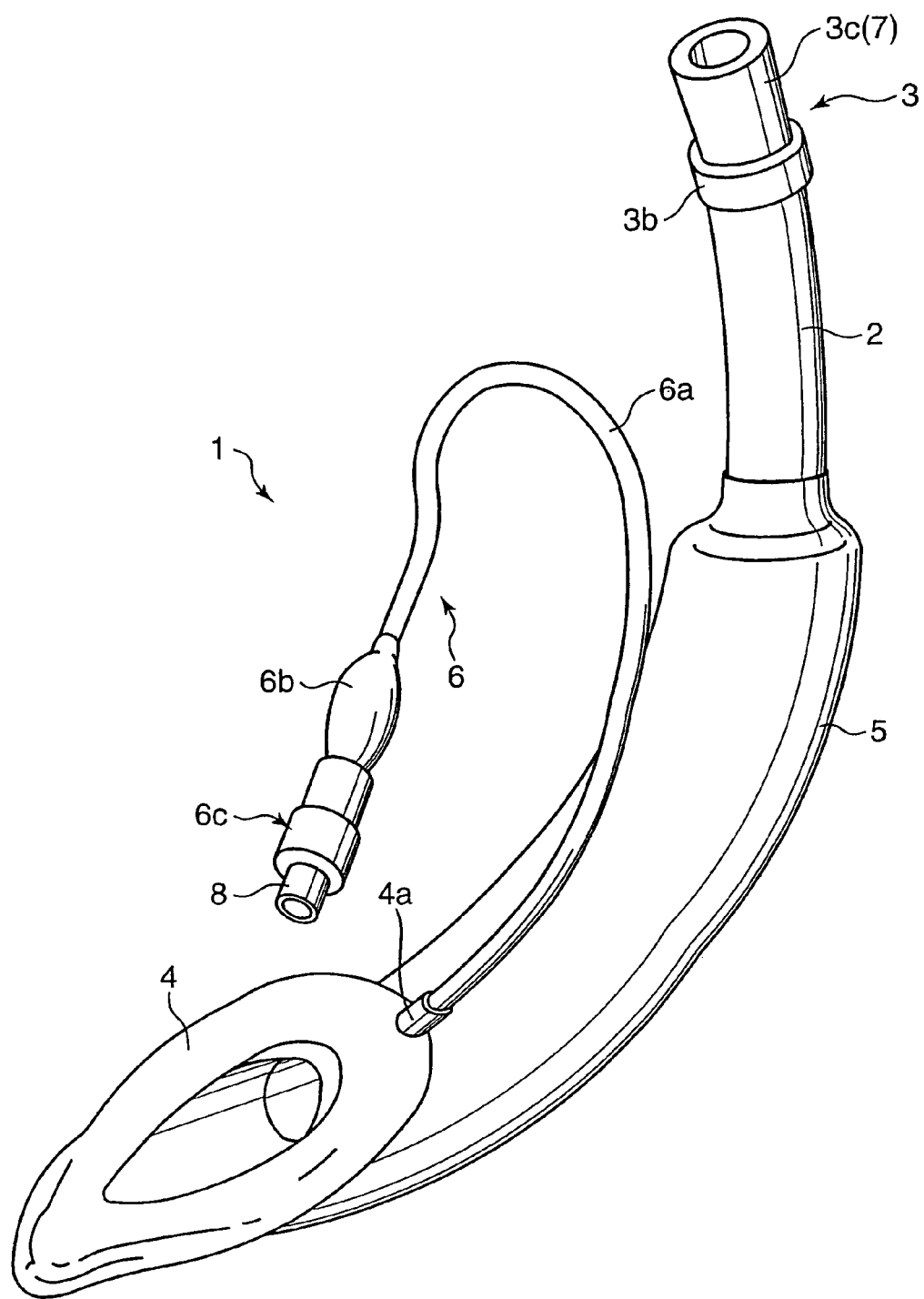
FIG. 1 is a perspective view of a laryngeal mask according to an embodiment of the present invention, showing its whole configuration.
Figure 2:
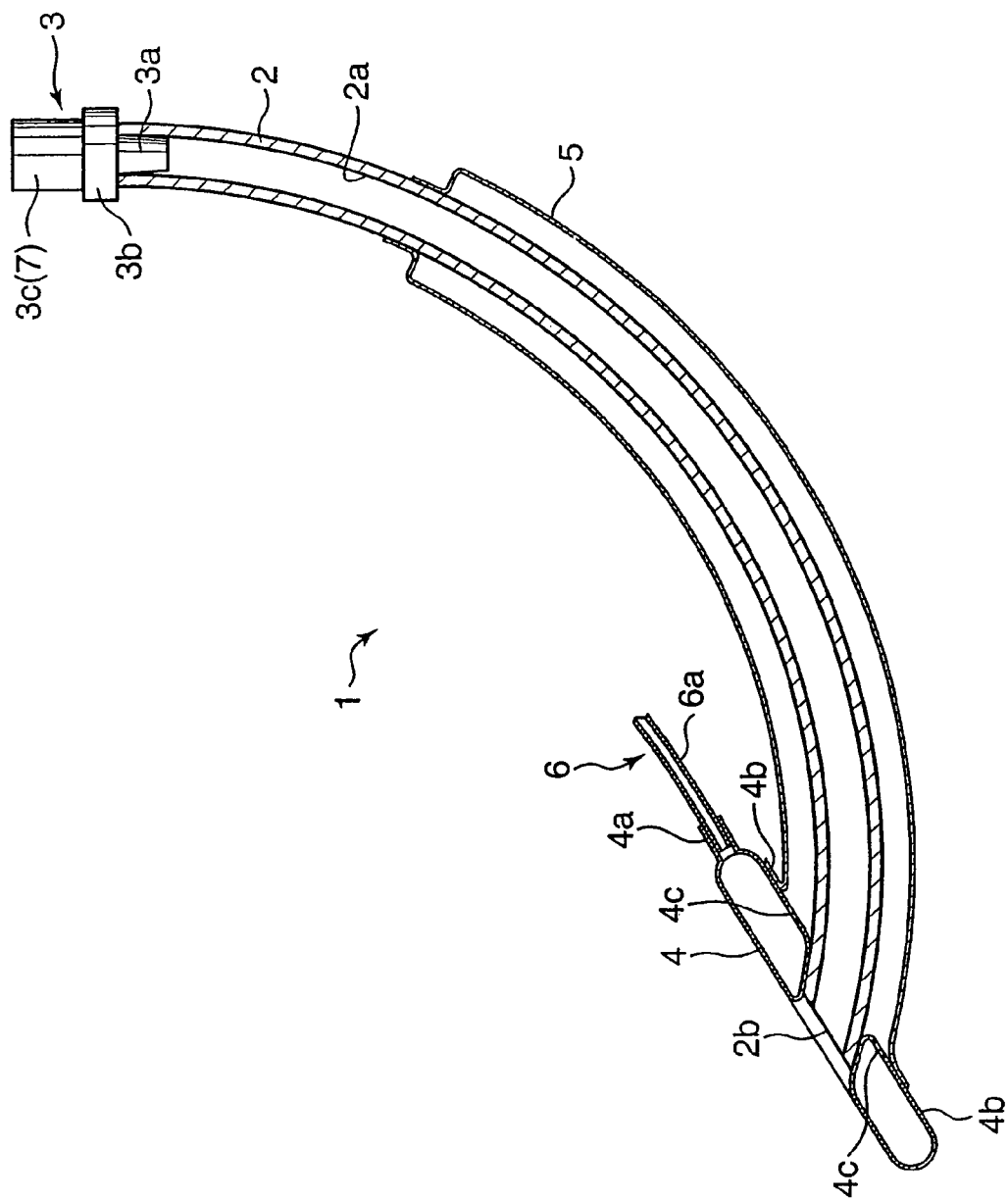
FIG. 2 is a side sectional view of the laryngeal mask in FIG. 1.
Figure 3:
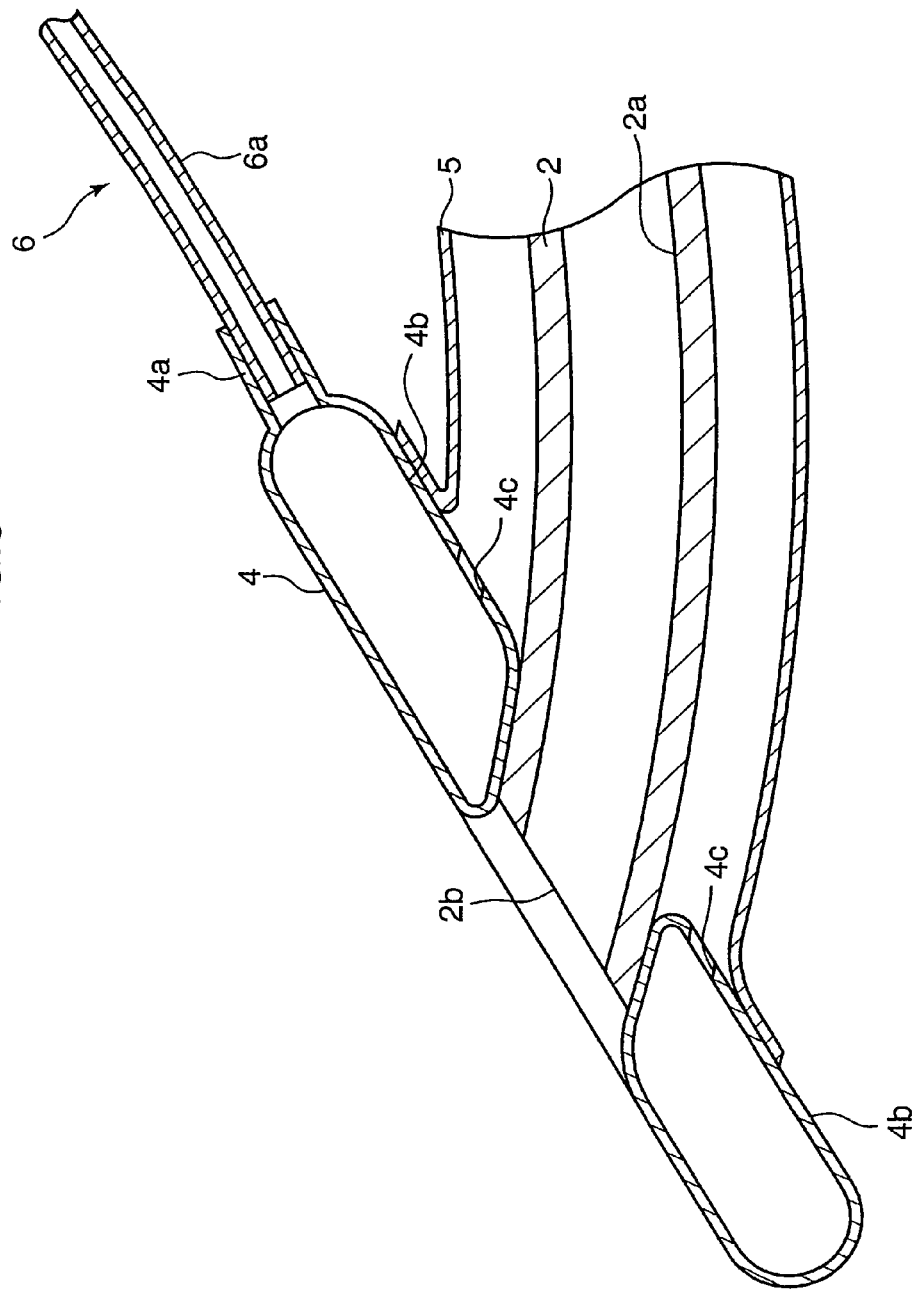
FIG. 3 is a schematic enlarged sectional partial view of the front-end part of the laryngeal mask in FIG. 2.

FIG. 1 is a perspective view of a laryngeal mask 1 according to an embodiment of the present invention, showing its whole configuration. FIG. 2 is a side sectional view of the laryngeal mask 1 in FIG. 1. FIG. 3 is a schematic enlarged sectional partial view of the front-end part of the laryngeal mask 1 in FIG. 2.

With reference to each figure, the laryngeal mask 1 includes: a tube body 2 which has a substantially arc shape; a connector 3 which is attached to the basic-end part of this tube body 2; a cuff 4 which is placed on an outer surface of the front-end part of the tube body 2; a pharyngeal cuff (or a storage portion) 5 which is the tube body 2 so the it extends from the cuff 4 toward the side of the basic-end part; and an injection and discharge portion 6 which can inject and discharge a fluid into and from both cuffs 4, 5.

The tube body 2 is made of a flexible resinous material such as flexible vinyl chloride, and a tube-shaped member which has a hollow portion 2a. The front-end part of the tube body 2 has an inclined end surface 2b which inclines toward the side of the basic-end part as it goes toward the central side of the arc shape.

The connector 3 is a tube-shaped member which is made of a relatively-rigid resinous material such as polyethylene. The connector 3 includes a narrow-diameter connection portion 3a, and a wide-diameter linkage portion 3c which is formed to be concentric with this connection portion 3a via a flange 3b.

The connection portion 3a is fitted into the hollow portion 2a of the tube body 2, so that its exterior circumferential surface and the interior circumferential surface of the tube body 2 can create an airtight state between them. In the linkage portion 3c, a tapered surface 7 is formed at its exterior circumferential surface. This tapered surface 7 is designed to have measurements so that the linkage portion 3c can be attached to, and detached from, a distributing pipe of an artificial respirator (not shown) or the like.

The cuff 4 is made of a flexible material such as a silicone resin. It is joined to the front-end peripheral part of the tube body 2, along the peripheral directions, so as to incline along the inclined end surface 2b of the tube body 2. The cuff 4 is hollow to store a fluid and is like a swimming ring as a whole.

In the side part of the cuff 4 on the side of the basic-end part, an attachment pipe 4a is formed which protrudes outward and leads inside. In this attachment pipe 4a, there is inserted a connection tube 6a of the injection and discharge portion 6. Both this connection tube 6a and the attachment pipe 4a are joined between the exterior circumferential surface of the former and interior circumferential surface of the latter. In an end wall 4b of the cuff 4 on the side of the basic-end part, a plurality of holes 4c which lead into the cuff 4 are formed along its peripheral directions.

The pharyngeal cuff 5 is a tube-shaped member which is made of a flexible material such as a silicone resin. The pharyngeal cuff 5 is joined at its front-end part to the end wall 4b of the cuff 4, and it is joined at its basic-end part to the peripheral surface of the tube body 2. Between these joint parts, a fluid can be stored between the tube body 2 and the pharyngeal cuff 5.

In the pharyngeal cuff 5, its front-end part is joined in a position outside of each hole 4c to the end wall 4b. Thereby, a fluid injected from the injection and discharge portion 6 is led through each hole 4c into the pharyngeal cuff 5.

The injection and discharge portion 6 is a structure in which the connection tube 6a joined to the cuff 4, a pilot balloon 6b and a valve body 6c are linked in series in this order. The valve body 6c includes a linkage portion 8 into which a syringe is fitted so that an airtight state can be created. If the syringe is inserted, a valve is opened, and the syringe is pulled out, the valve is closed. This configuration is publicly known, and thus, its detailed description is omitted herein.

If a fluid is injected into the cuff 4 and the pharyngeal cuff 5, the above described pilot balloon 6b inflates according to the internal pressure of the cuff 4 and the pharyngeal cuff 5. Then, a medical worker touches it and detects the internal pressure of both cuffs 4, 5.

Figure 4:
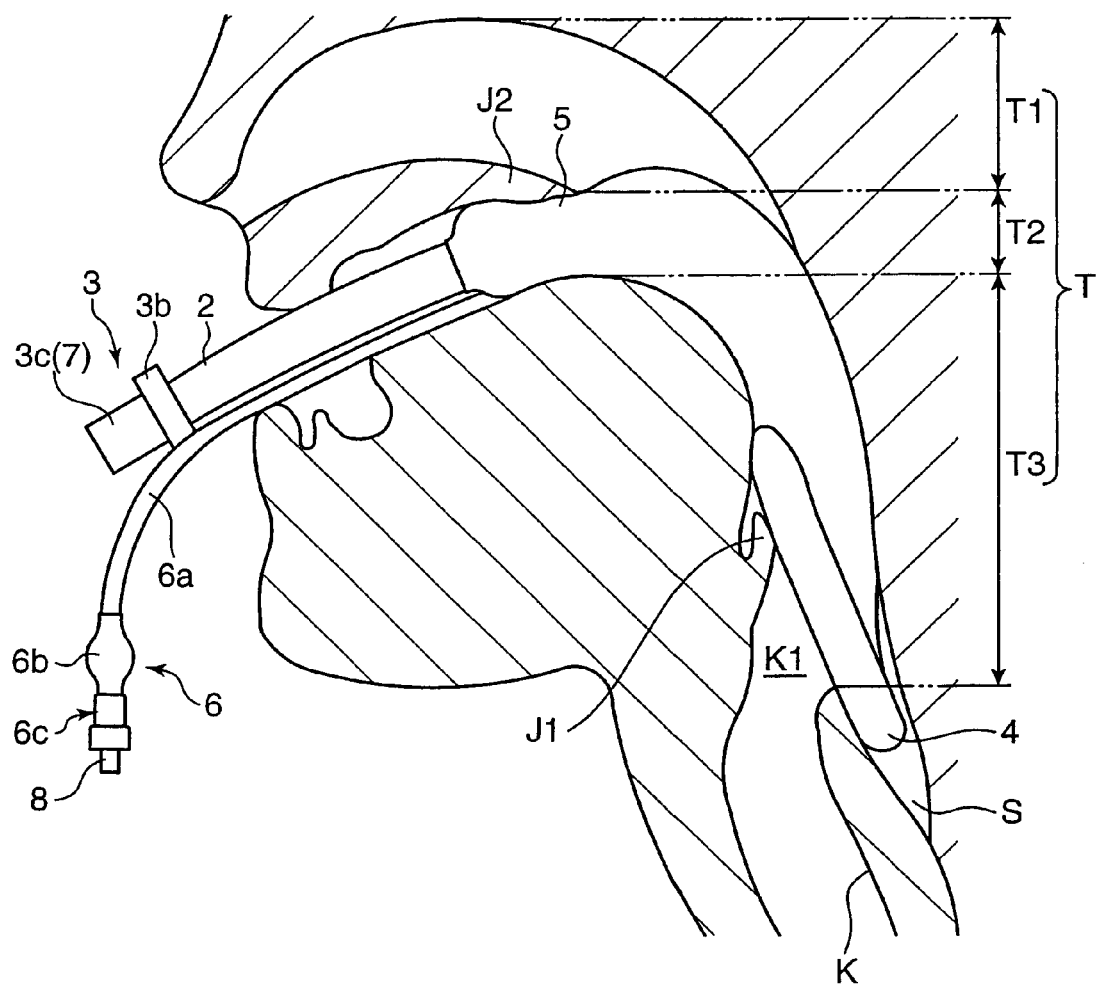
FIG. 4 is a schematic side sectional view of the laryngeal mask in FIG. 1, showing a state where it is fitted in a patient.

Hereinafter, how to use the laryngeal mask 1 will be described with reference to FIG. 4.

First, a medical worker inserts (or orally inserts) the tube body 2 into the mouth of a patient (i.e., a living body) from the side of the cuff 4. Then, the medical worker brings the cuff 4 up to the branching part of an esophagus S and a trachea K. Next, the medical worker injects a coolant (or a fluid which has a large quantity of specific heat: e.g., a fat emulsion) which has been cooled beforehand, into the cuff 4 and the pharyngeal cuff 5 from the valve body 6c of the injection and discharge portion 6. Consequently, both cuffs 4, 5 are inflated.

The inflated cuff 4 adheres at its front-end part closely to the inner wall of the esophagus, and its basic-end part adheres closely to the vicinity of an epiglottis J1. As a result, the cuff 4 adheres closely to the peripheral part of an opening part K1 of the trachea K. Therefore, a gas such as oxygen which is led through the connector 3 from an artificial respirator or the like passes through the hollow portion 2a of the tube body 2. Then, it is led into the trachea K.

On the other hand, the inflated pharyngeal cuff 5 extends backward from a palate J2 of a patient. It adheres closely to a mesopharynx T2 and a hypopharynx T3 in the peripheral directions. Herein, the description is given by regarding a pharyngeal part T as including three regions of: an epipharynx T1 which is located above the palate J2 that is contiguous to a nasal cavity; the mesopharynx T2 which you can see when a patient opens his/her mouth; and the hypopharynx T3 which is located above the inlet part of the esophagus S.

Then, a medical worker discharges the coolant from the injection and discharge portion 6, before he/she pulls the tube body 2 out of a patient.

As described hereinbefore, in the laryngeal mask 1, a coolant is injected into the pharyngeal cuff 5, with the tube body 2 kept inserted. This allows the pharyngeal cuff 5 to adhere closely to the pharyngeal part T. Thus, the pharyngeal part T can be cooled by the coolant which is cooled in the pharyngeal cuff 5. At and near this pharyngeal part T, there are numerous blood vessels which supply blood to the brain. Therefore, the pharyngeal cuff 5 cools these blood vessels, thereby cooling the blood in the blood vessels and cooling the brain.

Hence, in the laryngeal mask 1, the blood vessels which lie relatively close to the brain is cooled from the inside of the body. This allows the brain to cool within a short period of time. In addition, the brain is cooled via blood, and thus, it can be cooled adequately up to its sub-cortical tissue.

Furthermore, in the laryngeal mask 1, using the tube body 2, an airway is maintained in the respiratory tract of a living body. This makes it possible to simultaneously conduct a cardiac-arrest resuscitation treatment such as artificial respiration, and a hypothermic therapy.

Furthermore, in the laryngeal mask, the pharyngeal part T is cooled. Therefore, a contact area of the pharyngeal cuff 5 with respect to the pharyngeal part can be maintained large. On the other hand, in the case where an oral cuff which corresponds with the pharyngeal cuff 5 is inserted into an oral cavity or behind of the oral cavity, enough size of the contact area of the vessels with respect to the cuff cannot be maintained. Thus, it is difficult to obtain a cooling ability. On the other hand, the pharyngeal mask 1 has enough size of a contact area with respect to the vessels as compared with the case where the oral cavity or behind of the oral cavity is cooled. Therefore, a high cooling ability can be obtained.

According to the configuration where the pharyngeal cuff 5 is disposed to surround the tube body 2, the injected coolant inflates the pharyngeal cuff 5 in the peripheral directions of the tube body 2. This allows the pharyngeal cuff 5 to more certainly adhere closely to the pharyngeal part T.

According to the configuration where the cuff 4 is connected to the pharyngeal cuff 5, a coolant which is injected from the single injection and discharge portion 6 can be injected into both the cuff 4 and the pharyngeal cuff 5. Therefore, an operation for inflating the cuff 4 and an operation for inflating the pharyngeal cuff 5 can be conducted as a series of operations. This contributes to raising operational efficiency.

Herein, in the laryngeal mask 1, a fluid is injected into each of the cuff 4 and the pharyngeal cuff 5 from the injection and discharge portion 6. However, the configuration is not limited to this. For example, a laryngeal mask 10 may also be used as shown in FIG. 5 and FIG. 6.

Figure 5:
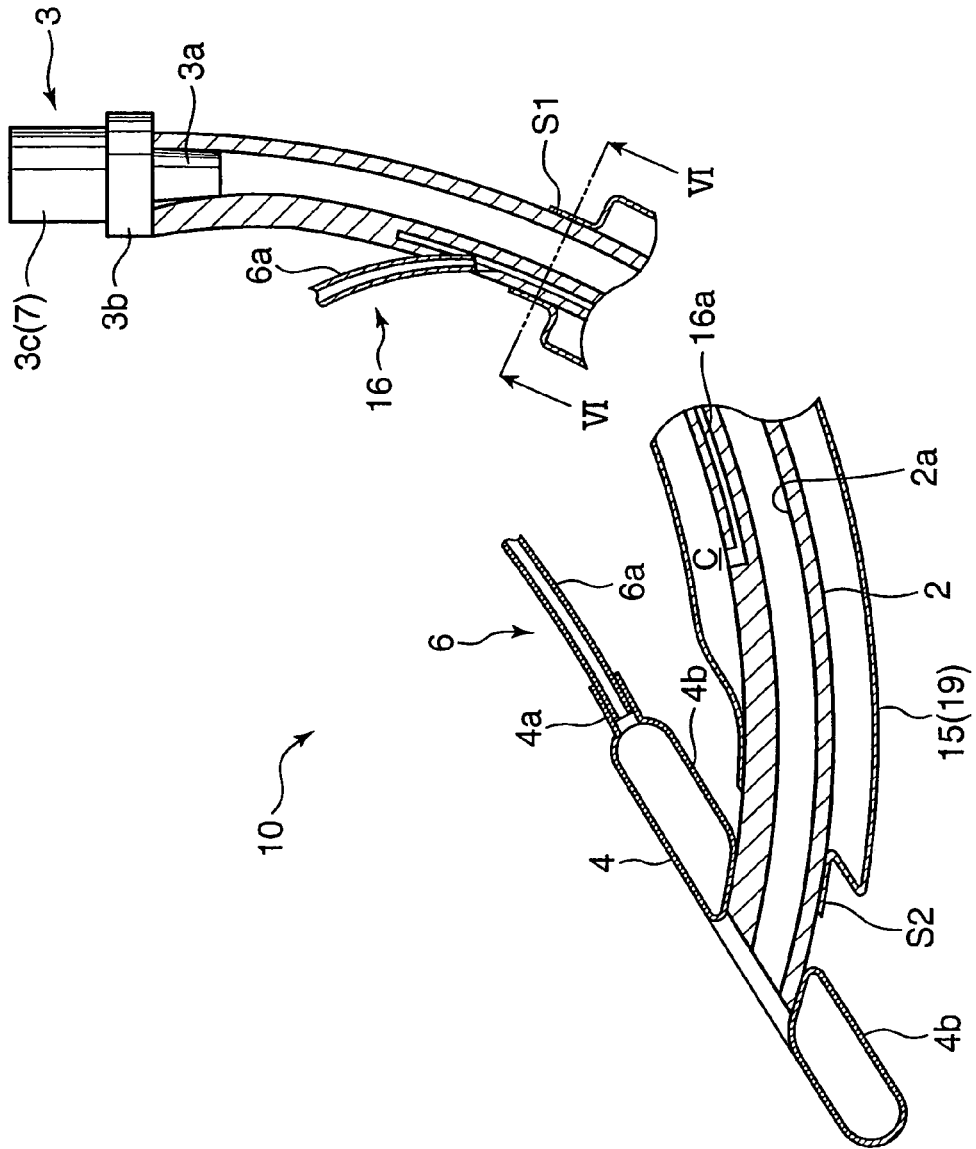
FIG. 5 is a partially-omitted side sectional view of a laryngeal mask according to another embodiment of the present invention.
Figure 6:
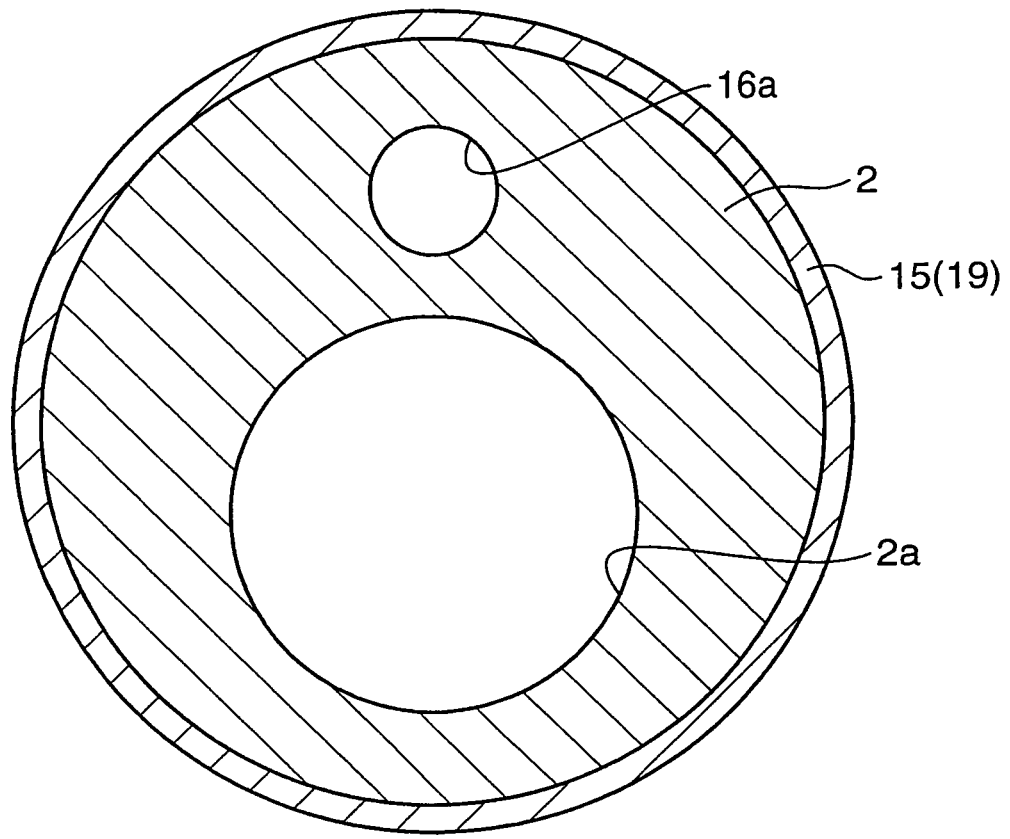
FIG. 6 is a sectional view of the laryngeal mask in FIG. 5, seen along a VI-VI line.

FIG. 5 is a partially-omitted side sectional view of the laryngeal mask 10 according to another embodiment of the present invention. FIG. 6 is a sectional view of the laryngeal mask in FIG. 5, seen along a VI-VI line. Herein, in the following description, if it has the same configuration as the above described laryngeal mask 1, the same reference numerals and characters are given, and thus, their description is omitted.

With reference to each figure, in the laryngeal mask 10, a pharyngeal cuff 15 is not connected to the cuff 4. In this respect, it is different from the one according to the above described embodiment (i.e., it has a configuration where the holes 4c of the cuff 4 are omitted).

Specifically, the laryngeal mask 10 includes a flexible tube 19 which is placed on an outer surface of the tube-shaped member along its longitudinal directions. This flexible tube 19 is joined to the peripheral surface of the tube body 2 along its peripheral directions, in two places (or joint places S1, S2) in the longitudinal directions. Thereby, the pharyngeal cuff 15 is formed outside of the tube body 2.

In the pharyngeal cuff 15, a coolant which is injected from an injection and discharge portion 16 is stored in a storage space C. Herein, the storage space C is formed between the joint places S1, S2 and between the tube body 2 and the flexible tube 19.

The injection and discharge portion 16 includes: a hole 16a which is formed in parallel with the hollow portion 2a inside of the tube body 2; the above described connection tube 6a which is connected to the hole 16a; the above described pilot balloon 6b; and the above described valve body 6c (refer to FIG. 1). In the hole 16a, its front-end part is open to the side of the tube body 2 so that it leads to the storage space C. On the other hand, its basic-end part is open to the side of the tube body 2 outside of the flexible tube 19. Into the opening part of this basic-end part, there is inserted the connection tube 6a. The connection tube 6a is joined to the tube body 2, so that the hollow part of the connection tube 6a leads to the hole 16a.

In this laryngeal mask 10, the cuff 4 is inflated so that an airway is maintained in the respiratory tract. In that state, the pharyngeal cuff 15 is inflated. In the same way as the one according to the above described embodiment, this allows the inflated pharyngeal cuff 15 to adhere closely to the mesopharynx T2 and the hypopharynx T3 of a patient.

Hence, according to this embodiment, the pharyngeal cuff 15 is formed by joining the flexible tube 19 to the tube body 2, in two places in its longitudinal directions. This makes the laryngeal mask 10 relatively low in price.

Furthermore, in this laryngeal mask 10, the injection and discharge portion 6 which is used for the cuff 4 and the injection and discharge portion 16 which is used for the pharyngeal cuff 15 are separately provided. This makes it possible to separately inflate and deflate the cuff 4 and the pharyngeal cuff 15.

Figure 7:
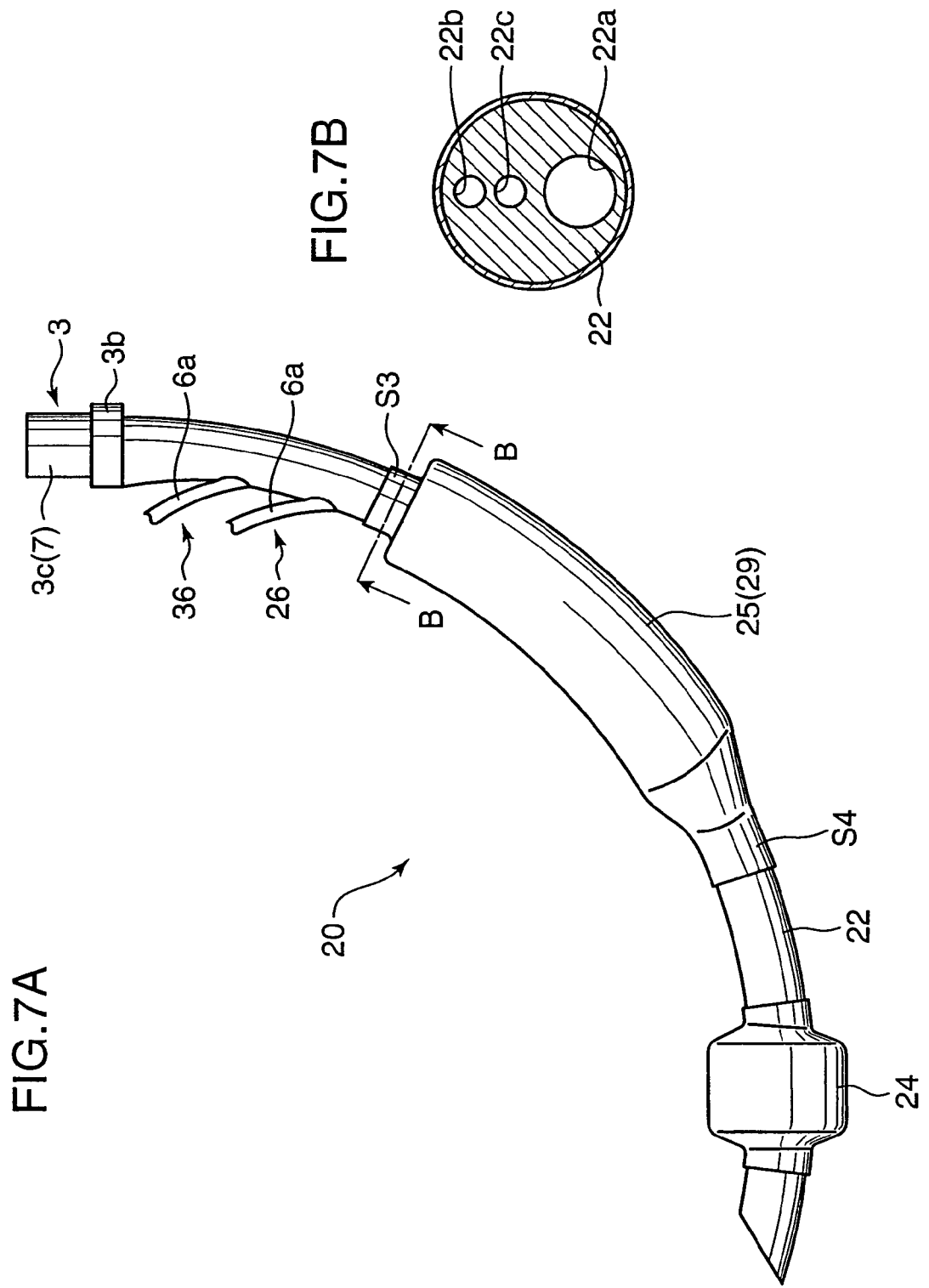
FIG. 7A is a side view of a tracheal tube according to still another embodiment of the present invention, showing its whole configuration.
FIG. 7B is a sectional view of the tracheal tube in FIG. 7A, seen along a B-B line.

Moreover, according to each embodiment, the above description has been given about the laryngeal masks 1, 10 which are provided with the pharyngeal cuffs 5, 15. However, the present invention is not limited to laryngeal masks. For example, as shown in FIG. 7, a pharyngeal cuff 25 may also be provided in a tracheal tube 20.

The tracheal tube 20 is used to maintain an airway in the respiratory tract of a patient. To do that, a tube body 22 thereof which has a substantially arc shape is orally inserted. Specifically, a cuff 24 which is provided at the front-end part of the tube body 22 in the tracheal tube 20 is inserted up to the inside of the trachea K (refer to FIG. 4) of a patient. In that state, air is injected from an injection and discharge portion 26 to inflate the cuff 24. Thereby, an airtight state is created between the peripheral surface of the cuff 24 and the trachea K. Thus, oxygen or the like which is led through the connector 3 from an artificial respirator is guided into the trachea K, through a hollow portion 22a of the tube body 22.

In the same way as the injection and discharge portion 16 (refer to FIG. 5) of the above described laryngeal mask 10, the injection and discharge portion 26 can inject and discharge a fluid into and from the cuff 24. This is conducted via a hole 22b which is formed in parallel with the hollow portion 22a inside of the tube body 22. Specifically, the injection and discharge portion 26 includes: the hole 22b; the connection tube 6a which is connected to this hole 22b; the above described pilot balloon 6b; and the above described valve body 6c (refer to FIG. 1).

In addition, the tracheal tube 20 includes a flexible tube 29 which is placed on an outer surface of the tube body 22 along its longitudinal directions. This flexible tube 29 is joined to the peripheral surface of the tube body 22 along its peripheral directions, in two places (or joint places S3, S4) in the longitudinal directions. Thereby, the pharyngeal cuff 25 is formed outside of the tube body 22.

In the pharyngeal cuff 25, a coolant which is injected from an injection and discharge portion 36 is stored between the joint places S3, S4 and between the tube body 22 and the flexible tube 29.

In the same way as the above described injection and discharge portion 16 (refer to FIG. 5), the injection and discharge portion 36 can inject and discharge a coolant into and from the cuff 24. This is conducted via a hole 22c which is formed in parallel with the hollow portion 22a inside of the tube body 22. Specifically, the injection and discharge portion 36 includes: the hole 22c; the connection tube 6a which is connected to this hole 22c; the above described pilot balloon 6b; and the above described valve body 6c (refer to FIG. 1).

Hence, in the tube body 22 of the tracheal tube 20 according to this embodiment, as shown in FIG. 7B, three holes are formed along its longitudinal directions; the hollow portion 22a and the holes 22b, 22c. The hollow portion 22a passes through the tube body 22 from the front-end part to the basic-end part thereof. In the hole 22b, its front-end part is open to the side of the tube body 22 so that it leads into the cuff 24. On the other hand, its basic-end part leads to the hollow part of the connection tube 6a of the injection and discharge portion 26. In the hole 22c, its front-end part is open to the side of the tube body 22 so that it leads into the pharyngeal cuff 25. On the other hand, its basic-end part leads to the hollow part of the connection tube 6a of the injection and discharge portion 36.

In this tracheal tube 20, the cuff 24 is inflated inside of the trachea K, so that an airway is maintained in the respiratory tract. In that state, the pharyngeal cuff 25 is inflated. In the same way as the one according to each embodiment, this allows the inflated pharyngeal cuff 25 to adhere closely to the mesopharynx T2 and the hypopharynx T3 of a patient.

Herein, in the tracheal tube 20, the cuff 24 and the pharyngeal cuff 25 are separately provided. However, the cuff 24 and the pharyngeal cuff 25 may also be connected, as is the case with the above described laryngeal mask 1 (refer to FIG. 1 to FIG. 3). In that case, a common injection and discharge portion may also be provided to both cuffs 24, 25.

Furthermore, according to this embodiment, the description has been given about the state in which the tracheal tube 20 is orally inserted. However, the present invention is not limited to this. The tracheal tube 20 may also be nasally inserted. In that case, the pharyngeal cuff 25 can cool the range from the epipharynx T1 to the hypopharynx T3.

Figure 8:
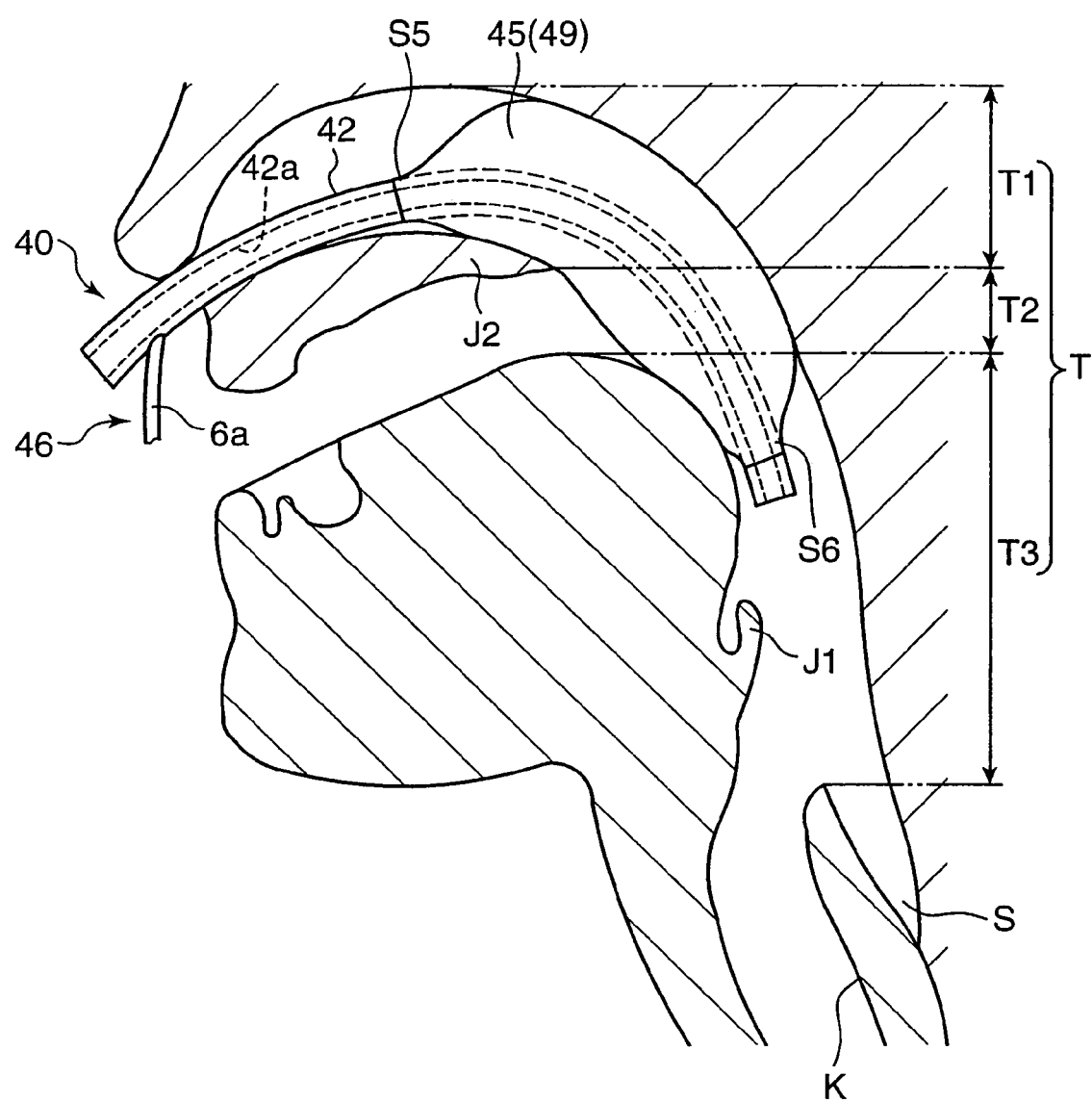
FIG. 8 is a schematic side sectional view of a nasal airway according to still another embodiment of the present invention, showing a state where it is fitted in a patient.

In addition to the one according to each embodiment, as shown in FIG. 8, a pharyngeal cuff 45 may also be provided in a nasal airway 40 which is nasally inserted.

The nasal airway 40 is used to maintain an airway in the respiratory tract of a patient. To do that, a tube body 42 thereof which has a substantially arc shape is nasally inserted. Specifically, the front-end part of the tube body 42 of the nasal airway 40 is placed within any range of the epipharynx T1 to the hypopharynx T3 of a patient. This gives an airway inside of the respiratory tract to a patient who cannot open the respiratory tract, or who is in such a state.

Besides, the nasal airway 40 includes a flexible tube 49 which is placed on an outer surface of the tube body 42 along its longitudinal directions. This flexible tube 49 is joined to the peripheral surface of the tube body 42 along its peripheral directions, in two places (or joint places S5, S6) in the longitudinal directions. Thereby, the pharyngeal cuff 45 is formed outside of the tube body 42.

In the pharyngeal cuff 45, a coolant which is injected from an injection and discharge portion 46 is stored between the tube body 42 and the flexible tube 49.

In the same way as the above described injection and discharge portion 16 (refer to FIG. 5), the injection and discharge portion 46 can inject and discharge a coolant into and from the cuff 45. This is conducted via a hole (not shown) which is formed in parallel with a hollow portion 42a inside of the tube body 42. Specifically, the injection and discharge portion 46 includes: this hole; the connection tube 6a which is connected to the hole; the above described pilot balloon 6b; and the above described valve body 6c (refer to FIG. 1).

In the nasal airway 40 which is configured in this way, the pharyngeal cuff 45 is allowed to adhere to the range from the epipharynx T1 to the hypopharynx T3.

Figure 9A:
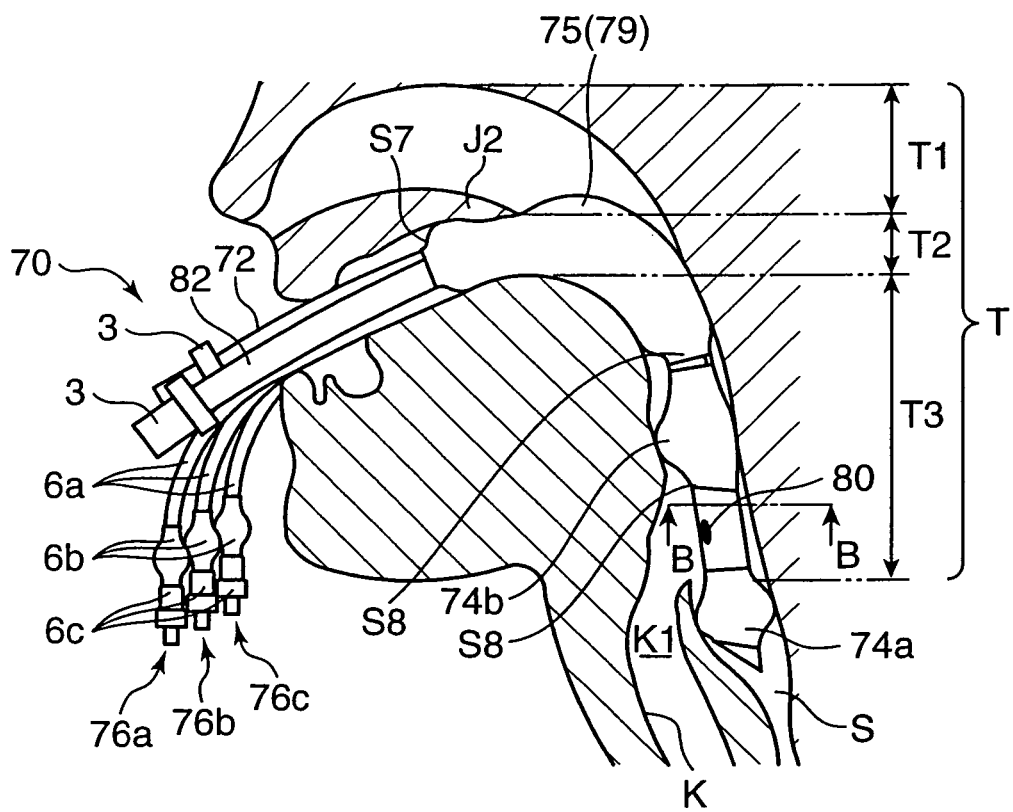
FIG. 9A is a schematic side sectional view of an esophagus-closing two-hollow tube according to still another embodiment of the present invention, showing a state where it is fitted in a patient.
Figure 9B:
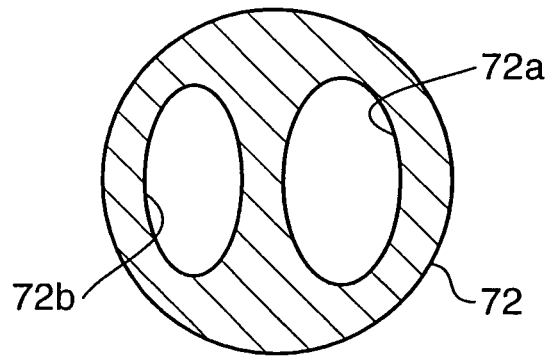
FIG. 9B is a sectional view of the esophagus-closing two-hollow tube in FIG. 9A, seen along a B-B line.

Furthermore, a pharyngeal cuff 75 may also be provided in such an esophagus-closing two-hollow tube 70 as shown in FIG. 9.

The esophagus-closing two-hollow tube 70 (hereinafter, referred to as the two-hollow tube 70) is used to maintain an airway in the respiratory tract of a patient. To do that, a tube body 72 thereof which has a substantially arc shape is orally inserted.

Specifically, a cuff 74a which is provided at the front-end part of the tube body 72 in the two-hollow tube 70 is inserted up to the esophagus S of a patient. In that state, air is injected from an injection and discharge portion 76a to inflate the cuff 74a. Thereby, an airtight state is created between the peripheral surface of the cuff 74a and the esophagus S. When the cuff 74a is placed inside of the esophagus S, a cuff 74b which is provided on the tube body 72 is placed at and near the hypopharynx T3. Into this cuff 74b, air is injected through an injection and discharge portion 76b, so that the cuff 74b is inflated. This inflation creates an airtight space between both cuffs 74a, 74b. Inside of this space, there is located the opening part K1 of the trachea K.

In the tube body 72, there are formed a first hollow portion 72a which penetrates through from the basic-end part to the front-end part thereof, and a second hollow portion 72b which extends from between both cuffs 74a, 74b to the side of the basic-end part. In this second hollow portion 72b, its front-end part is open, through a hole 80, to the side of the tube body 72. On the other hand, its basic-end part leads to a second tube body 82.

In the second tube body 82, in the same way as the connection tube 6a (refer to FIG. 5) of the above described injection and discharge portion 16, its front-end part is inserted into the second hollow portion 72b which is open to the side of the tube body 72 on its basic-end part side. Then, the second tube body 82 is joined to the tube body 72, so that the second hollow portion 72b leads to the hollow part of the second tube body 82. The second tube body 82 is provided with the connector 3 which is linked to its basic-end part. Via this connector 3, oxygen or the like which is introduced from an artificial respirator passes through the second hollow portion 72b of the tube body 72 and the hole 80. Then, it is led into the trachea K.

Herein, the two-hollow tube 70 can be used even in a state where the front-end part (i.e., the cuff 74a) of the tube body 72 is inserted into the trachea K. In that case, an artificial respirator is linked to the connector 3 which is linked to the basic-end part to the tube body 72. Thereby, oxygen or the like which is introduced from the artificial respirator is guided into the trachea K, through the first hollow portion 72a.

Besides, the two-hollow tube 70 according to this embodiment includes a flexible tube 79 which is placed on an outer surface of the tube body 72 along its longitudinal directions. This flexible tube 79 is joined to the peripheral surface of the tube body 72 along its peripheral directions, in two places (or joint places S7, S8) in the longitudinal directions. Thereby, the pharyngeal cuff 75 is formed outside of the tube body 72.

In the pharyngeal cuff 75, a coolant which is injected from an injection and discharge portion 76c is stored between the tube body 72 and the flexible tube 79.

In the same way as the above described injection and discharge portion 16 (refer to FIG. 5), the injection and discharge portion 76c can inject and discharge a coolant into and from the cuff 75. This is conducted via a hole (not shown) which is formed in parallel with each hollow portion 72a, 72b inside of the tube body 72. Specifically, the injection and discharge portion 76c includes: this hole; the connection tube 6a which is connected to the hole; the above described pilot balloon 6b; and the above described valve body 6c.

In the two-hollow tube 70 which is configured in this way, the pharyngeal cuff 75 is allowed to adhere to the range of the mesopharynx T2 and the hypopharynx T3.

Herein, in the two hollow tube 70, the cuff 74b and the pharyngeal cuff 25 are separately provided. However, the cuff 74b and pharyngeal cuff 25 may be united.

In the above described laryngeal mask 10, tracheal tube 20, nasal airway 40 and two-hollow tube 70, the pharyngeal cuffs 15, 25, 45 and 75 are united to the tube bodies 2, 22, 42 and 72, respectively. However, the configuration is not limited to this.

For example, each tube body 2, 22, 42 and 72 may also be configured separately from its corresponding pharyngeal cuff 15, 25, 45 and 75.

In that case, the pharyngeal cuffs 15, 25, 45 and 75 are shaped like a hollow container having a hole into which each tube body 2, 22, 42 and 72 can be inserted. In addition, an injection and discharge portion is provided which can inject a coolant into each pharyngeal cuff 15, 25, 45 and 75. The pharyngeal cuffs 15, 25, 45 and 75 which are configured in this way can be inserted up to the pharyngeal part along the tube bodies 2, 22, 42 and 72 which have already been inserted.

The present invention has the object of bringing the pharyngeal cuffs 15, 25, 45 and 75 into contact with the pharyngeal part T over a wide area, thus cooling the pharyngeal part T, and thereby keeping ischemic neuronal damage under control. In view of this object, it is preferable that the pharyngeal cuffs 15, 25, 45 and 75 be continuously formed along the longitudinal directions and the peripheral directions of the tube bodies 2, 22, 42 and 72, as is the case according to each embodiment. However, the configuration is not necessarily limited to this. The pharyngeal cuffs 15, 25, 45 and 75 may also be intermittent formed in the peripheral directions or the longitudinal directions of the tube bodies 2, 22, 42 and 72. According to this configuration, the pressure which is exerted on the pharyngeal part T can be made lower. This allows a medical worker to suitably choose from among those configurations of the pharyngeal cuffs 15, 25, 45 and 75, according to the condition of a patient.

Hereinafter, with reference to FIG. 10 and FIG. 11, a fluid injection apparatus 50 will be described which can inject a coolant which has been cooled into the above described laryngeal mask 1, 10, tracheal tube 20, nasal airway 40 and two-hollow tube 70.

Figure 10:
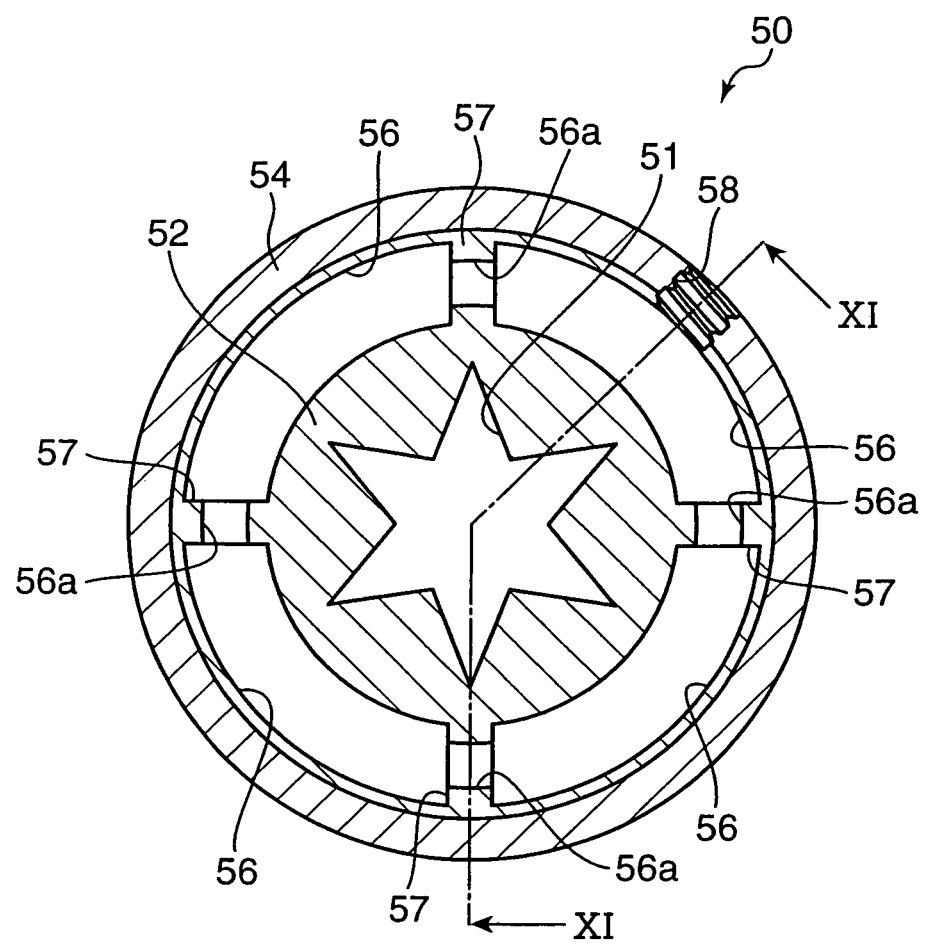
FIG. 10 is a front sectional view of a fluid injection apparatus which injects a coolant into a pharyngeal cuff.

FIG. 10 is a front sectional view of the fluid injection apparatus 50 which injects a coolant into the pharyngeal cuffs 5, 15, 25, 45 and 75. FIG. 11 is a sectional view of the fluid injection apparatus 50 in FIG. 10, seen along an XI-XI line.

With reference to each figure, the fluid injection apparatus 50 includes: a main-body portion 52 which has a storage chamber 51 inside that can store a coolant; a pressuring member 53 which applies pressure to a coolant that is stored in the storage chamber 51; and an insulating member 54 which is placed on an outer surface of the main-body portion 52. When you push the pressuring member 53 into the main-body portion 52, a coolant inside of the storage chamber 51 is discharged outside through a discharge port (or a discharge portion) 55 of the main-body portion 52.

The main-body portion 52 is a columnar member which is made of a material that has a relatively high heat-radiation rate, such as aluminum. In its axial directions, the discharge port 55 protrudes which has a cylindrical shape. In this main-body portion 52, the storage chamber 51 which has a sectional shape like a substantially six-point star leads to a hollow portion 55a of the discharge port 55, along the axis of the main-body portion 52. Herein, the discharge port 55 has a peripheral-surface shape (which is similar to a syringe) so that it can be fitted in an airtight state into the linkage portion 8 of the valve body 6c.

In addition, in the main-body portion 52, a coolant storage chamber (or a coolant storage portion) 56 is formed which encircles the storage chamber 51 around its axis. This coolant storage chamber 56 has a sectional shape like a doughnut and is a space which is formed along the axial directions of the main-body portion 52. It is divided around the axis into four spaces by wall portions 57. In each wall portion 57, a hole 56a is formed which allows two adjacent spaces of the coolant storage chamber 56 to lead to each other. These holes 56a make any two adjacent spaces of the coolant storage chamber 56 leading to each other.

Besides, in the side surface of the main-body portion 52, an internal-thread portion 58 is formed which makes one division space of the coolant storage chamber 56 open to the outside through the insulating member 54. Onto this internal-thread portion 58, a bottle B which stores a liquefied $CO_2$ gas can be screwed at an outlet B2 thereof.

The pressuring member 53 includes a piston 59 which can rub and move upon the wall surface that demarcates the storage chamber 51, and a plunger 60 which is connected to this piston 59. The piston 59 has a front shape like a substantially six-point star, so that it can create a liquid-tight state with the wall surface that demarcates the storage chamber 51. The plunger 60 extends from the piston 59 up to the outside of the main-body portion 52, so that it can push the piston 59 toward the side of the discharge port 55.

The insulating member 54 is made of an insulating material such as a urethane resin, and is fixed on the peripheral surface of the main-body portion 52.

When a medical worker uses the fluid injection apparatus 50, first, he/she pulls the plunger 60 up, so that a coolant is sucked from the discharge port 55 into the storage chamber 51. In this state, the medical worker links the outlet B2 of the bottle B of a liquefied $CO_2$ gas to the internal-thread portion 58. Thereby, the liquefied $CO_2$ gas fills the coolant storage chamber 56, thus lowering the temperature of the coolant storage chamber 56. The cold energy which has been generated by lowering the temperature is transferred to the main-body portion 52. However, it is mainly transferred not to the outside of the main-body portion 52, but to the side of the storage chamber 51. This is because the insulating member 54 is disposed on the outside of the main-body portion 52. The storage chamber 51 is demarcated by its wall part which is shaped like a substantially six-point star. This makes its heat-transfer area larger than in the case where it has a circular wall part, thus heightening its coefficient of heat transfer.

Then, the medical worker stands by for a predetermined period of time and confirms that the coolant has been cooled. Thereafter, he/she links the discharge port 55 to the linkage portion 8 of the valve body 6c, and pushes the valve plunger 60 toward the side of the main-body portion 52. Thereby, the coolant which has been cooled is injected into the pharyngeal cuffs 5, 15, 25 and 45.

Figure 11:
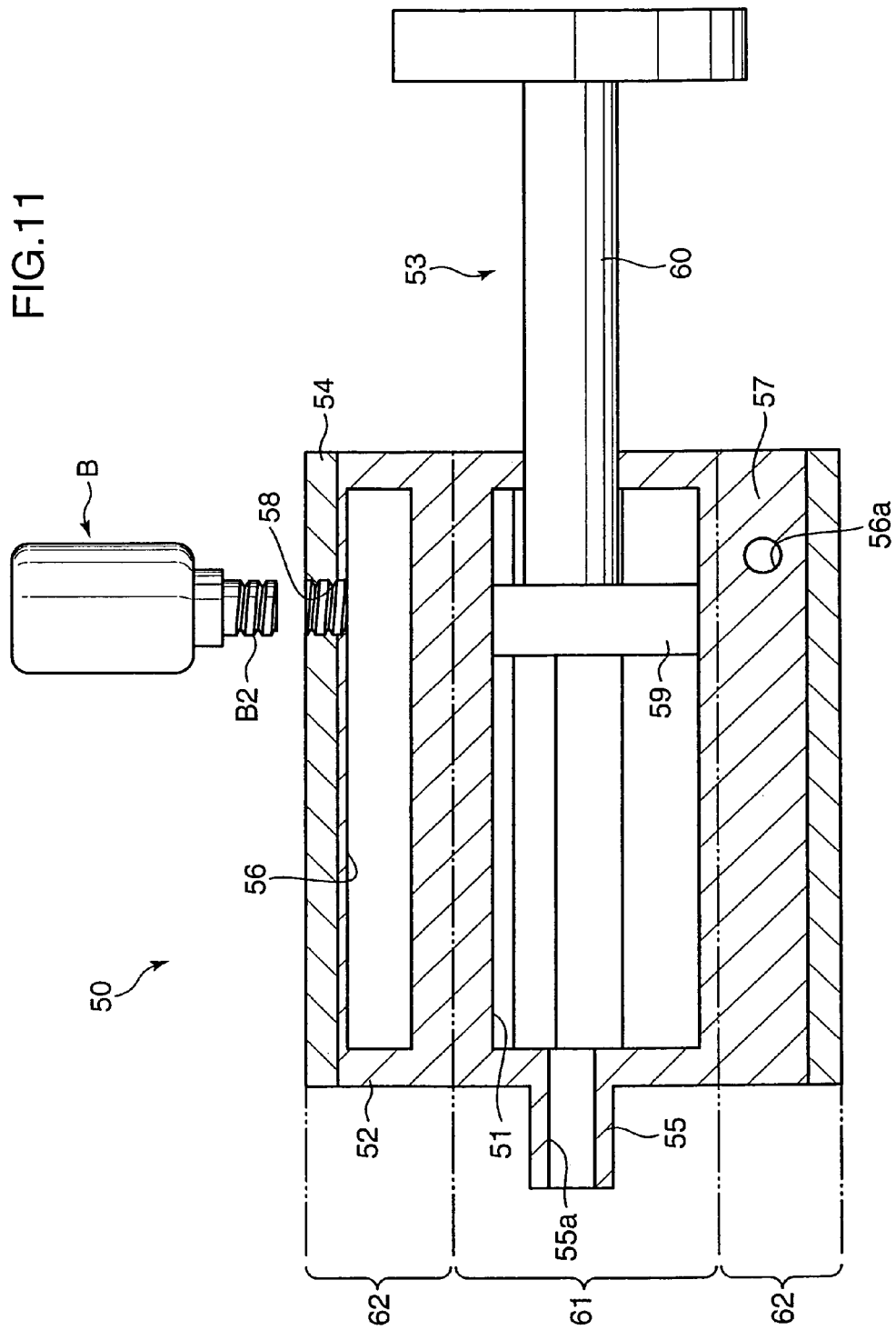
FIG. 11 is a sectional view of the fluid injection apparatus in FIG. 10, seen along an XI-XI line.

Herein, in the fluid injection apparatus 50, as shown by a virtual line in FIG. 11, the main-body portion 52 is described which is formed, as an example, by uniting a fluid storage portion 61 that stores a coolant and a cooling portion 62 that cools a coolant inside of this fluid storage portion 61. However, these fluid storage portion 61 and cooling portion 62 may also be separately formed.

As described above, in the fluid injection apparatus 50, the cooling portion 62 is provided, and thus, after a coolant inside of the fluid storage portion 61 is cooled, the coolant can be injected into the above described laryngeal mask 1, 10, tracheal tube 20, nasal airway 40 and two-hollow tube 70.

According to the configuration where the cooling portion 62 is provided with the coolant storage chamber 56, this coolant storage chamber 56 is filled with a liquefied $CO_2$ gas. This makes it possible to cool a fluid inside of the fluid storage portion 61.

Herein, in the fluid injection apparatus 50, a liquefied $CO_2$ gas is filled into the coolant storage chamber 56. However, the configuration is not limited to this. For example, two kinds of chemical substances may also be used whose temperature will be lower after they are mixed. In that case, they are filled after being mixed. Or, one of those chemical substances before they are mixed is filled in advance into the coolant storage chamber 56, and thereafter, the other chemical substance is injected. Or, a wall part which divides the coolant storage chamber 56 in two is further provided, so that the two kinds of chemical substances can be separately stored. If this wall part is broken, those chemical substances are mixed in the coolant storage chamber 56.

In addition, as described earlier, a fat emulsion is mentioned as an example of the coolant. However, the coolant may also be suitably selected out of fluids which are harmless to patients. Among such fluids, preferably, it should be selected out of fluid which has a large quantity of specific heat. If you take specific heat into account, it is preferable that those fluids be selected out of liquids.

As described above, a brain cooling apparatus according to the present invention comprises: a tube-shaped member which is orally and nasally inserted so that an airway is maintained in the respiratory tract of a living body; a storage portion which is attached to the peripheral part of the tube-shaped member and stores a cooled fluid; and an injection and discharge portion which injects and discharges a fluid into and from the storage portion, wherein the storage portion is flexible enough to inflate and deflate when a fluid is injected and discharged, and when a fluid is injected in a state where an airway in the respiratory tract of a living body is maintained by the tube-shaped member, the inflated storage portion adheres closely to the pharyngeal part of the living body.

According to the above described configuration, a fluid is injected into the storage portion, with the tube-shaped member kept inserted in a living body. This allows the storage portion to adhere closely to the pharyngeal part. Thus, the pharyngeal part can be cooled by the cooled fluid inside of the storage portion. At and near the pharyngeal part, there are numerous blood vessels which supply blood to the brain. Therefore, the storage portion cools these blood vessels, thereby cooling the blood in the blood vessels and cooling the brain.

Hence, according to the above described configuration, the blood vessels which lies relatively close to the brain is cooled from the inside of the body (i.e., the pharyngeal part). This allows the brain to cool within a short period of time. In addition, the brain is cooled via blood, and thus, it can be cooled adequately up to its sub-cortical tissue.

Furthermore, according to the above described configuration, the brain is cooled by cooling only the pharyngeal part. Therefore, cares about when to cool the brain become smaller than in the case where the whole body is cooled.

Furthermore, according to the above described configuration, using the tube-shaped member, an airway is maintained in the respiratory tract of a living body. This makes it possible to simultaneously conduct a cardiac-arrest resuscitation treatment such as artificial respiration, and a hypothermic therapy.

In the above described brain cooling apparatus, preferably, the storage portion surrounds the peripheral part of the tube-shaped member in the peripheral directions thereof.

According to the configuration where the storage portion is disposed to surround the tube-shaped member, the injected fluid inflates the storage portion in the peripheral directions of the tube-shaped member. This allows the storage portion to adhere closely to the pharyngeal part more certainly.

In the above described brain cooling apparatus, preferably, a flexible tube is place on an outer surface of the tube-shaped member; the storage portion is formed by joining the flexible tube to the peripheral surface of the tube-shaped member along the peripheral directions thereof, in two parts in the longitudinal directions; and between these joint parts, a fluid is stored between the flexible tube and the tube-shaped member.

According to the configuration where the flexible tube is provided, the storage portion is formed by joining the flexible tube to the tube-shaped member, in two parts in the longitudinal directions. This makes the cooling apparatus relatively low in price.

In the above described brain cooling apparatus, preferably, the tube-shaped member is provided, at the peripheral part of the front-end thereof, with a cuff which inflates by storing a fluid that is injected from the injection and discharge portion; and the storage portion is connected to the cuff so that it receives a fluid which is injected into the cuff, and extends from the cuff toward the side of the basic-end part of the tube-shaped member, along the axial direction of the tube-shaped member.

According to the configuration where the storage portion is connected to the cuff which is formed at the peripheral part of the front-end part of the tube-shaped member, a fluid which is injected from the single injection and discharge portion can be injected into both the cuff and the storage portion. Therefore, an operation for inflating the cuff and an operation for inflating the storage portion can be conducted as a series of operations. This contributes to raising operational efficiency.

In the above described brain cooling apparatus, preferably, the tube-shaped member is a tube body of a laryngeal mask, and the front-end part thereof is orally inserted up to the branching part of the esophagus and trachea of a living body.

According to the configuration where the storage portion is provided in the tube body of a laryngeal mask, the laryngeal mask blocks the side of the esophagus selectively, so that an airway is maintained in the respiratory tract of a living body. At the same time, the pharyngeal part can be cooled by the storage portion formed in the tube body. Herein, the laryngeal mask is equipment which an emergency life-saving technician is authorized to use. Thus, it can be used effectively in an emergency situation where an airway should be maintained in the respiratory tract.

In the above described brain cooling apparatus, preferably, the tube-shaped member is a tube body of a tracheal tube, and the front-end part thereof is orally and nasally inserted up to the inside of the trachea of a living body.

According to the configuration where the storage portion is provided in the tube body of a tracheal tube, the tracheal tube is inserted into the trachea, so that an airway is maintained in the respiratory tract of a living body. At the same time, the pharyngeal part can be cooled by the storage portion formed in the tube body.

In the above described brain cooling apparatus, preferably, the tube-shaped member is a tube body of a nasal airway which is nasally inserted.

According to the configuration where the storage portion is provided in the tube body of a nasal airway, the nasal airway which is nasally inserted helps maintain an airway in the respiratory tract of a living body which is difficult to open or the like. At the same time, the pharyngeal part can be cooled by the storage portion formed in the tube body.

In the fluid injection apparatus which can inject a fluid into the above described brain cooling apparatus, the cooling portion is provided, and thus, a fluid which is stored in the fluid storage portion is cooled and then the fluid is injected into the cooling apparatus.

According to the fluid injection apparatus which can inject a fluid into the above described brain cooling apparatus, a cooling portion is provided, and thus, after a coolant inside of the fluid storage portion is cooled, the coolant can be injected into the cooling apparatus.

In the above described fluid injection apparatus, preferably, the cooling portion is disposed to surround the outside of the fluid storing portion, includes a refrigerant storage portion which fills up with a refrigerant, and cools a fluid by transferring the cold energy of the refrigerant to the fluid storage portion.

According to the configuration where the cooling portion is provided with the refrigerant storage portion, the refrigerant storage portion is filled with a refrigerant (e.g., a liquefied $CO_2$ gas), so that a fluid in the fluid storage portion can be cooled.

According to the present invention, a fluid is injected into the storage portion, with the tube-shaped member kept inserted in a living body. This allows the storage portion to adhere closely to the pharyngeal part. Thus, the pharyngeal part can be cooled by the cooled fluid inside of the storage portion. At and near the pharyngeal part, there are numerous blood vessels which supply blood to the brain. Therefore, the storage portion cools these vessels, thereby cooling the blood in the blood vessels and cooling the brain.

The invention claimed is:

1. A brain cooling apparatus, comprising:
   a tube-shaped member which is orally or nasally inserted so that an airway is maintained in the respiratory tract of living body;
   a storage portion which is attached to the peripheral part of the tube-shaped member and stores a cooled fluid;
   an injection and discharge portion which injects and discharges a fluid into and from the storage portion; and
   a cuff attached to the peripheral part of a front end of the tube-shaped member,
   wherein the storage portion and the cuff are flexible enough to inflate and deflate when a fluid is injected and discharged, and are such that when a fluid is injected, the cuff is configured to adhere closely to a peripheral part of an opening part of a trachea such that an airway in the respiratory tract of living body is maintained by the tube-shaped member, and the inflated storage portion is configured to adhere closely to the pharyngeal part of the living body;
   wherein the cuff is configured to inflate by storing a fluid that is injected from the injection and discharge portion; and
   wherein the storage portion is connected to the cuff so that the storage portion receives a fluid which is injected into the cuff, and extends from the cuff toward the side of the basic-end part of the tube-shaped member, along the axial direction of the tube-shaped member.

2. The brain cooling apparatus according to claim 1, wherein the storage portion surrounds the peripheral part of the tube-shaped member in the peripheral directions thereof.

3. The brain cooling apparatus according to claim 2, wherein:
   a flexible tube is placed on an outer surface of the tube-shaped member;
   the storage portion is formed by joining the flexible tube to the peripheral surface of the tube-shaped member along the peripheral directions thereof, in two parts in the longitudinal directions; and
   between these joint parts, a fluid is stored between the flexible tube and the tube-shaped member.

4. The brain cooling apparatus according to claim 1, wherein the tube-shaped member is a tube body of a laryngeal mask, and the front-end part thereof is orally inserted up to the branching part of the esophagus and trachea of a living body.

5. A fluid injection apparatus which injects a fluid into the brain cooling apparatus according to claim 1, comprising:
   a discharge portion which is attached to the injection and discharge portion;
   a fluid storage portion which stores a fluid that is discharged from the discharge portion; and
   a cooling portion which cools a fluid that is stored in the fluid storage portion.

6. The fluid injection apparatus according to claim 5, wherein the cooling portion is disposed to surround the outside of the fluid storage portion, includes a refrigerant storage portion which fills up with a refrigerant, and cools a fluid by transferring the cold energy of the refrigerant to the fluid storage portion.

7. The brain cooling apparatus according to claim 2, wherein the tube-shaped member is a tube body of a laryngeal mask, and the front-end part thereof is orally inserted up to the branching part of the esophagus and trachea of a living body.

8. The brain cooling apparatus according to claim 3, wherein the tube-shaped member is a tube body of a laryngeal mask, and the front-end part thereof is orally inserted up to the branching part of the esophagus and trachea of a living body.

9. A fluid injection apparatus which injects a fluid into the brain cooling apparatus according to claim 2, comprising:
   a discharge portion which is attached to the injection and discharge portion;
   a fluid storage portion which stores a fluid that is discharged from the discharge portion; and
   a cooling portion which cools a fluid that is stored in the fluid storage portion.

\* \* \* \* \*